United States Patent
Scialdone

(10) Patent No.: US 7,435,851 B2
(45) Date of Patent: Oct. 14, 2008

(54) PULEGANIC AMIDES

(75) Inventor: Mark A. Scialdone, West Grove, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/541,057

(22) Filed: Sep. 29, 2006

(65) Prior Publication Data

US 2007/0077263 A1 Apr. 5, 2007

Related U.S. Application Data

(60) Provisional application No. 60/722,663, filed on Sep. 30, 2005, provisional application No. 60/722,806, filed on Sep. 30, 2005.

(51) Int. Cl.
*C07C 233/58* (2006.01)
*A01N 25/00* (2006.01)
*A01N 43/40* (2006.01)
*A01N 37/18* (2006.01)

(52) U.S. Cl. .............. 564/189; 514/237.5; 514/227.5; 514/255.01; 514/317; 514/613; 544/59; 544/172; 544/396; 546/226; 424/405

(58) Field of Classification Search ........... 514/613, 514/255.01, 237.5, 227.5, 317; 564/189; 546/226; 544/59, 172, 396
See application file for complete search history.

(56) References Cited

U.S. PATENT DOCUMENTS 3,225,290 A 12/1965 Grist
4,021,224 A * 5/1977 Pallos et al. .............. 504/112

2003/0062357 A1 4/2003 Schneider et al.
2003/0079786 A1 5/2003 Diana et al.
2003/0191047 A1 10/2003 Hallahan
2006/0148842 A1 7/2006 Scialdone et al.

FOREIGN PATENT DOCUMENTS

WO WO 03/079786 A1 10/2003

OTHER PUBLICATIONS

Curran et al, Tetrahedron, vol. 50, No. 25, 7343-7366, 1994.*
Eisner, Catnip: Its Raison D'Etre, Science Magazine, 1964, vol. 146:1318-1320.
Larock, Carboxylic Acids to Amides, Comprehensive Organic Transformations, 1989, pp. 972-976, VCH Publishers, Inc.
W. C. Still et. al., Rapid Chromatographic Technique for Preparative Separations With Moderate Resolutions, J. Org. Chemistry, 1978, vol. 43:2923-2925.
Curran, Radical Translocation Reactions of o-Iodoanilides: The Use of Carbon Hydrogen Bonds as Precursors of Radicals Adjacent to Carbonyl Groups, J. Org. Chem., 1991, vol. 56:4335-4337.
Curran, Amide-Based Protecting/Radical Translocating (PRT) Groups. Generation of Radicals Adjacent to Carbonyls By 1,5-Hydrogen Transfer Reactions of o-Iodoanilides, Tetrahedron, 1994, vol. 50:7343-7366.
Sakan et. al., The Exact Nature of Matatabilactone and the Terpenes of Nepeta Cataria, Tetrahedron Lett., 1965, pp. 4097-4101, No. 46.
J. F. Eijman, 2-Isopropyl-5Methyl-Cyclopentanecarboxyl, Chem. Zentralbl, 1911, vol. 82:1029, XP002417023.
International Search Report and the Written Opinion of the International Searching Authority, PCT/US2006/038092, Feb. 20, 2007.
Written Opinion of the International Searching Authority in PCT/US2006/038092, Feb. 20, 2007.

* cited by examiner

*Primary Examiner*—Shailendra Kumar

(57) ABSTRACT

The present invention provides substituted puleganic amides and compositions thereof, which are both useful as a topical treatment for skin, such as a repellant for insects and arthropods.

41 Claims, 2 Drawing Sheets

Repellency of diethyl puleganic amide (Ia) vs. DEET at 1% w/v.

Repellency of 2-methyl-piperidine puleganic amide (Ib) vs. DEET at 1% w/v.

PULEGANIC AMIDES

This application claims the benefit of U.S. Provisional Application No. 60/722,663, filed Sep. 30, 2005, and U.S. Provisional Application No. 60/722,806, filed Sep. 30, 2005, each of which is incorporated in its entirety as a part hereof for all purposes.

TECHNICAL FIELD

The present invention relates to substituted puleganic amides and compositions thereof. The uses of such compounds and compositions include use as a topical treatment of skin, such as a repellant for an insect or arthropod.

BACKGROUND

Insect repellents are used globally as a means of reducing human-insect vector contact, thereby minimizing the incidence of vector-borne disease transmission as well as the general discomfort associated with insect bites.

The best known and most widely used active ingredient in commercial topical insect repellents is the synthetic benzamide derivative, N,N-diethyltoluamide (DEET). DEET, however, exhibits several characteristics that are perceived as undesirable, such as an unpleasant odor and a greasy feel on the skin.

Alternatives to DEET as an insect repellant have been found in materials that can be derived from catmint oil, such as nepetalactone [as described in Eisner, *Science* (1964) 146: 1318-1320] and dihydronepetalactone (as described by Hallahan in WO 03/79786 and U.S. Ser. No. 03/225,290). There nevertheless exists a continuing need to provide low-cost and efficacious insect repellents, particularly those that can be derived from natural sources.

SUMMARY

In one embodiment, this invention provides substituted puleganic amides represented generally by the schematic structure of Formula I:

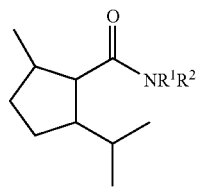

I wherein $R^1$ and $R^2$ are each independently selected from the group consisting of:
a) H, $CH_3$, $C_2H_5$;
b) a $C_3$ to $C_{20}$ straight-chain, branched or cyclic alkane or alkene group;
c) a $C_3$ to $C_{20}$ straight-chain, branched or cyclic alkane or alkene group comprising a heteroatom selected from the group consisting of O, N and S;
d) an unsubstituted or substituted $C_6$ to $C_{20}$ aromatic group, wherein the substituent is selected from the group consisting of a $C_1$ to $C_{12}$ straight-chain, branched or cyclic alkane or alkene group; and
e) an unsubstituted or substituted $C_6$ to $C_{20}$ aromatic group comprising a heteroatom selected from the group consisting of O, N and S, wherein the substituent is selected from the group consisting of a $C_1$ to $C_{12}$ straight-chain, branched or cyclic alkane or alkene group;

provided that $R^1$ and $R^2$ are not both hydrogen; and provided that $R^1$ and $R^2$ may optionally together form a cyclic or bicyclic alkanyl or alkenyl group unless the puleganic amide so formed is N-methyl-N-phenyl puleganic amide.

In another embodiment, this invention relates to a composition of matter comprising a compound of Formula I. The composition may comprise, in addition to the compound of Formula I, one or more of a carrier, a cosmetic or therapeutic adjuvant and an additional insect/arthropod repellant such as dihydronepetalactone.

In a further embodiment, this invention relates to a method for repelling insects and/or arthropods comprising exposing the insects and/or arthropods to a compound of the above described Formula I or a composition thereof.

In yet another embodiment, this invention relates to a method for method making a composition of matter that may be applied to the skin, hide, hair, feathers or fur or other surface of a human or domesticated animal by admixing (a) one or both of a carrier and a cosmetic or therapeutic adjuvant with (b) a compound described generally by the above described Formula I.

DETAILED DESCRIPTION

Figure 1:
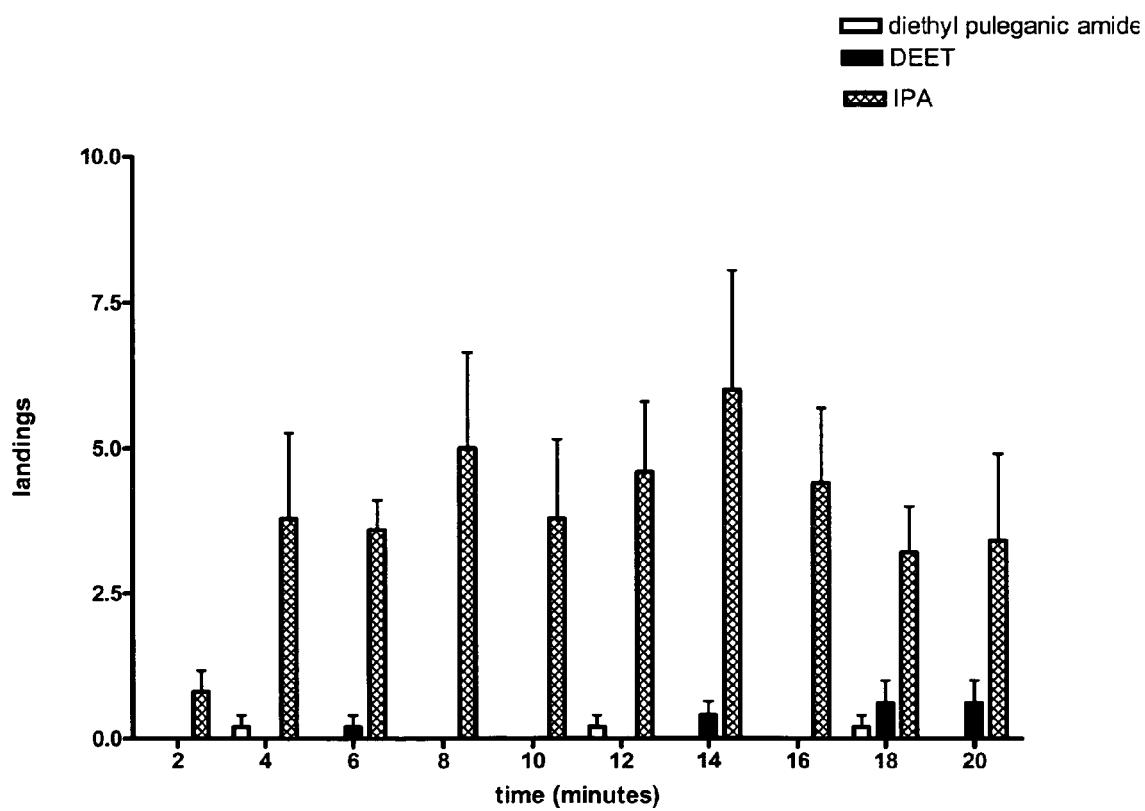
FIGS. 1 and 2 show the results of testing the indicated compounds of this invention against the indicated controls for their effect on the probing behavior of *Aedes aegypti* mosquitoes in the in vitro landing assay procedure, described herein. The horizontal scale shows time in minutes, and the vertical scale shows mean number of landings of mosquitoes.

Although a puleganic amide can be prepared as a derivative of nepetalactone, its use, and the use of derivatives thereof, for the purpose of repelling insects and/or arthropods has not been previously reported. As a result, this invention relates to puleganic amides, compositions of puleganic amides, and to the use of puleganic amides and compositions thereof as a topical treatment for skin such as a repellant for insects and arthropods.

Puleganic acid, as the term is used herein, is 2-isopropyl-5-methylcyclopentane carboxylic acid, and is described generally by the structure of Formula IV:

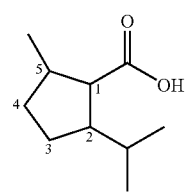

I

Puleganic acid suitable for use in this invention as an intermediate may be prepared using nepetalactone as the starting material. Nepetalactone, which is described generally by the structure of Formula II,

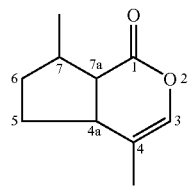

II may be obtained from the essential oil of the Nepeta (catmint) plant, such as the species *Nepeta Cataria*. The Nepeta plant leaves a preferred source of the raw material as nepetalactone is present in large quantity and may be readily purified therefrom. The essential oil of the catmint plant may be obtained by the steam distillation of the herbaceous plant material, and one of the primary isomers of nepetalactone, trans, cis-nepetalactone (shown in Formula IIa), can be purified from catmint oil via crystallization using petroleum ether-hexanes.

In addition to trans, cis-nepetalactone (IIa), another primary isomer of nepetalactone is cis, trans-nepetalactone (shown in Formula IIb), which has the (S)-configuration at the 7-carbon (according to the numbering scheme of the above Formula II), the methyl-bearing carbon on the cyclopentyl ring:

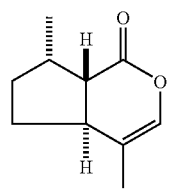

IIa

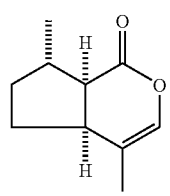

IIb

When hydrogenated, nepetalactone produces a mixture of puleganic acid and dihydronepetalactone ("DHN"). DHN, which is described generally by the structure of Formula III, may exist as either a single diastereomer or as a combination of diastereomers:

III

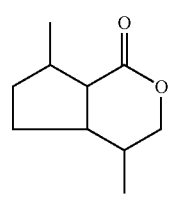

The structures of 9S dihydronepetalactone stereoisomers are shown below.

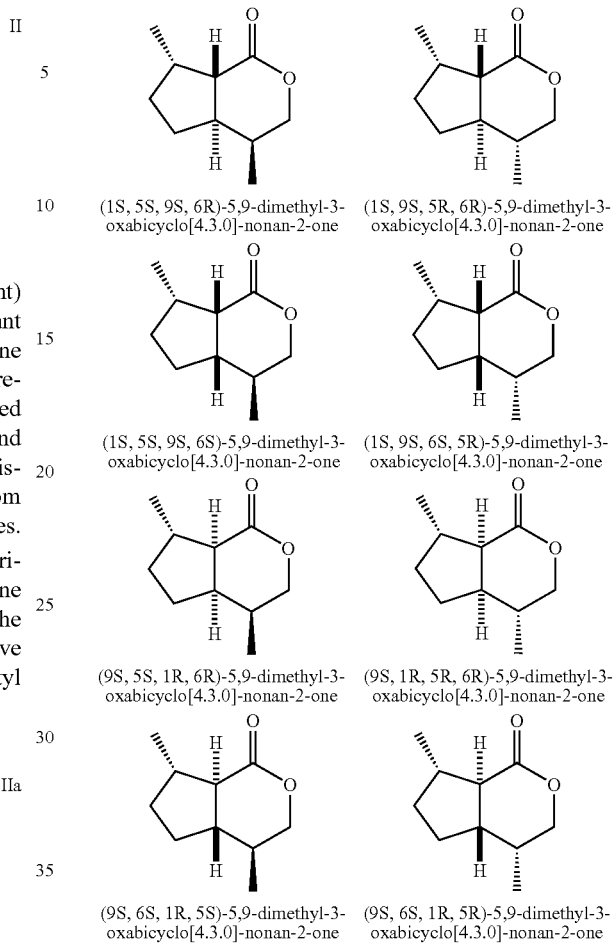

(1S, 5S, 9S, 6R)-5,9-dimethyl-3-oxabicyclo[4.3.0]-nonan-2-one (1S, 9S, 5R, 6R)-5,9-dimethyl-3-oxabicyclo[4.3.0]-nonan-2-one (1S, 5S, 9S, 6S)-5,9-dimethyl-3-oxabicyclo[4.3.0]-nonan-2-one (1S, 9S, 6S, 5R)-5,9-dimethyl-3-oxabicyclo[4.3.0]-nonan-2-one (9S, 5S, 1R, 6R)-5,9-dimethyl-3-oxabicyclo[4.3.0]-nonan-2-one (9S, 1R, 5R, 6R)-5,9-dimethyl-3-oxabicyclo[4.3.0]-nonan-2-one (9S, 6S, 1R, 5S)-5,9-dimethyl-3-oxabicyclo[4.3.0]-nonan-2-one (9S, 6S, 1R, 5R)-5,9-dimethyl-3-oxabicyclo[4.3.0]-nonan-2-one The reaction in which puleganic acid is formed by the hydrogenation of nepetalactone may be represented generally by the scheme of Reaction I, as follows:

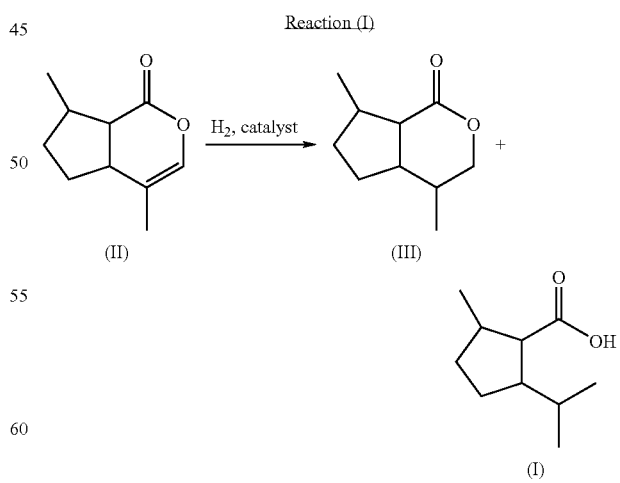

The hydrogenation of nepetalactone may be effected in the presence of a catalyst, i.e. a substance that affects the rate of the reaction but not the reaction equilibrium, and emerges from the reaction chemically unchanged. In a preferred embodiment, a supported metal hydrogenation catalyst is used. Suitable catalysts, supports and reaction conditions for this hydrogenation reaction are described in Manzer, U.S. Ser. No. 03/225,290 [4 Dec. 03 (which is incorporated in its entirety as a part hereof for all purposes)], particularly in Paragraphs 33 through 130 and Table 1 thereof. Exemplary catalysts that yield high amounts of puleganic acid include platinum- and iridium-based catalysts. Manzer demonstrates, for example, catalysts and conditions under which the reduction of trans, cis-nepetalactone (IIa) to dihydronepetalactone (IIIa) and puleganic acid (IVa), as shown generally in the scheme of Reaction (II), may be obtained:

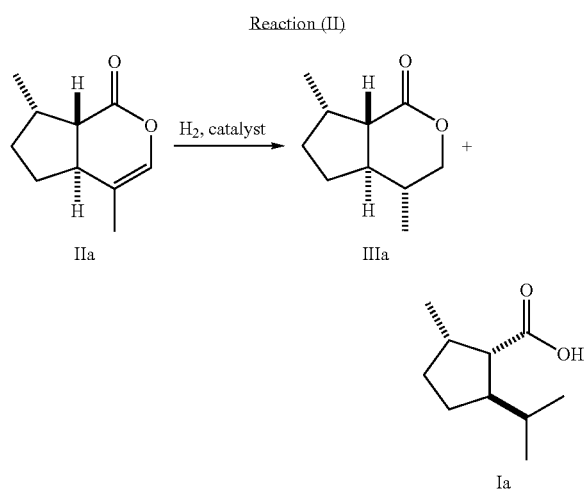

Puleganic acid may be purified from the mixture of products obtained from the hydrogenation of nepetalactone by liquid/liquid bicarbonate extraction, followed by acidification. Suitable organic solvents for this extraction include dichloromethane and chloroform.

The puleganic amides of this invention can be derived from puleganic acid diastereomers as a single stereoisomer or as a combination of stereoisomers. As nepetalactone may exist as discrete stereochemical isomers found in nature, puleganic acid derived from nepetalactone hydrogenation may also exist as diastereomers, such as those described generally by the Formulae IVa~IVd:

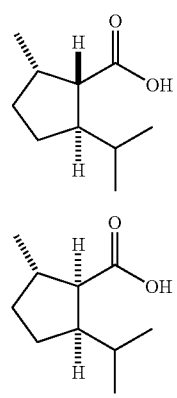

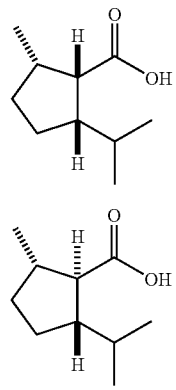

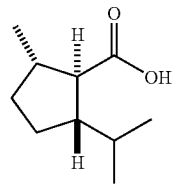

In addition to the stereoisomers of puleganic acid shown above in FIGS. IVa~IVd, which have the S configuration at the 5 carbon (according to the numbering scheme in Formula IV, i.e. the methyl-bearing carbon on the cyclopentyl ring), stereoisomers of puleganic acids having the R configuration at the 5 carbon are also useful in this invention as intermediates from which to prepare puleganic amides. For example, puleganic amides are derived from puleganic acid stereoisomer IVa (1S,2R,5S)-2-isopropyl-5-methylcyclopentanecarboxamide formed in the hydrogenation of trans, cis-nepetalactone (IIa).

Methods for converting carboxylic acids to carboxamides are well known and described, for example, in *Comprehensive Organic Transformations*, Richard C. Larock, VCH Publishers, Inc., NY, 1989, pages 972-976. Puleganic amides (Formula Ia) may be formed from puleganic acid (Formula IVa) by reaction of the acid chloride of puleganic acid with amines, as shown in Reaction (III):

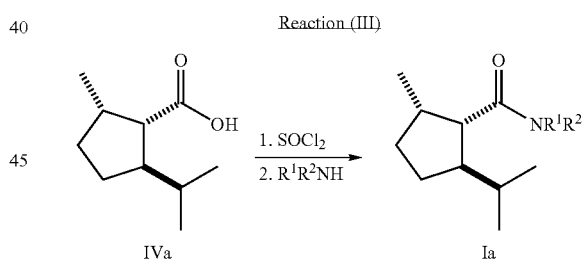

The amines used can also contain stereogenic centers and be chiral, such as 2-methylpiperidine used in Example 2 as a racemate, which is a combination of the (2S)-methyl- and (2R)-methyl-piperidine enantiomers. The use of such amines in the coupling procedure described in Reaction (III) generates diastereoisomeric puleganic amides.

Puleganic amides may be purified from the intermediate reactant puleganic acid by bicarbonate liquid/liquid extraction. Separation of the organic layer followed by evaporation of the solvent affords the crude puleganic amide products. Further purification is possible using flash by silica gel chromatography, as described in W. C. Still et al, Rapid Chromatographic Technique for Preparative Separations with Moderate Resolution, *J. Org. Chemistry* (1978), 43(14): 2923-2925.

Two amides of puleganic acid are known: puleganic amide (2-isopropyl-5-methyl-cyclopentanecarboxylic acid amide)

[Wallach, Terpenes and Ethereal Oils, CXI. I., Carvenolide and Pulegenolide, *Justus Liebigs Ann. Chem.* (1913) 392:49-59]; and N-methyl-N-phenyl puleganic amide [Curran, *J. Org. Chem.* (1991) 56:4335-4337; and Curran, Tetrahedron (1994) 50:7343-7366].

Puleganic amide compounds suitable for use in this invention may be represented generally by the following structural Formula I:

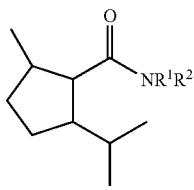

Formula I wherein $R^1$ and $R^2$ are each independently selected from the group consisting of:
1) H, $CH_3$, $C_2H_5$;
2) a $C_3$ to $C_{20}$, preferably $C_3$ to $C_{12}$, straight-chain, branched or cyclic alkane or alkene group;
3) a $C_3$ to $C_{20}$, preferably $C_3$ to $C_{12}$, straight-chain, branched or cyclic alkane or alkene group comprising a heteroatom selected from the group consisting of O, N and S;
4) an unsubstituted or substituted $C_6$ to $C_{20}$, preferably $C_6$ to $C_{12}$, aromatic group, wherein the substituent is selected from the group consisting of a $C_1$ to $C_{12}$ straight-chain, branched or cyclic alkane or alkene group; and
5) an unsubstituted or substituted $C_6$ to $C_{20}$, preferably $C_6$ to $C_{12}$, aromatic group comprising a heteroatom selected from the group consisting of O, N and S, wherein the substituent is selected from the group consisting of a $C_1$ to $C_{12}$ straight-chain, branched or cyclic alkane or alkene group;

provided that $R^1$ and $R^2$ are not both hydrogen; and provided that $R^1$ and $R^2$ may optionally together form a cyclic or bicyclic alkanyl or alkenyl group unless the puleganic amide so formed is N-methyl-N-phenyl puleganic amide.

In a preferred embodiment, the substituted puleganic amide of the invention is selected from the group consisting of N,N-diethyl-(1S,2R,5S)-2-isopropyl-5-methylcyclopentanecarboxamide, or [(±)-2-methylpiperidinyl]-(1S,2R,5S)-2-isopropyl-5-methylcyclopentane-carboxamide.

As indicated above, nepetalactone, dihydronepetalactone, plueganic acid and puleganic amides may all exist in diastereomeric form. As a result, unless stated to the contrary, a reference to a compound by its name, such as "puleganic amide", "puleganic acid", "nepetalactone" or "dihydronepetalactone", or a reference to a stereochemically ambiguous structure, will be interpreted to be an inclusive reference to any single stereoisomer thereof, and/or to any combination of any of, and/or to all of, the stereoisomers of these compounds. Mixtures of stereoisomers may thus be formed in which the molar or mass content of any individual stereoisomer, or any subgroup of the mixture, relative to the whole mixture can be variable.

This invention relates to puleganic amides as described above, to compositions comprising puleganic amides, and to the use of puleganic amides and the compositions thereof. The preparations of this invention, which include the puleganic amide compounds described above, and the compositions, formulations and other materials that may be prepared from such compounds according to this invention, and mixtures thereof, may all be used for a multiplicity of purposes. These purposes include, for example, use as an active ingredient in an effective amount for the repellency of various insect or arthropod species, use as a fragrance compound itself or as an ingredient in a perfume composition, or use as a topical treatment for skin.

For example, the preparations hereof may be applied in a topical manner to the skin, hide, hair, fur, feathers or other surface of a mammal, such as a human or domesticated animal, that serves as a host for an insect or arthropod. Living, animate hosts such as these may serve as insect-acceptable food sources for blood-feeding insects and arthropods such as biting flies, chiggers, fleas, mosquitoes, ticks and lice.

The preparations hereof may also be applied to or incorporated into an inanimate host for an insect or arthropod, which includes for example a food source such as growing or harvested plants or crops, or a desirable habitat such as a building or structure, or other types of protective articles such as may be made from fabrics or textiles. Such inanimate hosts may include, for example, towers, silos, bins, hoppers, boxes and bags in which food products such as grain is stored, which may be an attractive habitat or food source for insects such as flour or bean beetles or weevils. A preparation hereof may be used to repel such insects by applying the preparation to a container or article or to any point of access thereto.

The preparations hereof may also be applied to the skin and/or hair of humans to impart a pleasant odor or aroma as a fragrance compound itself, or as an ingredient in a perfume composition; and the preparations hereof may also be used as a topical treatment for skin by application to the skin and/or hair of humans in the form of a body wash, rinse, conditioner, toner, lotion, splash, spray or other type of cosmetic product as applied personally by the user.

A repellent substance drives insects or arthropods away from their preferred hosts, whether animate or inanimate, or renders those hosts unacceptable in some manner. Most repellents are not active poisons, but rather make desirable insect/arthropod hosts, or the conditions associated with those hosts, unattractive or offensive. Typically, a repellent is a preparation that can be topically applied to, on or about a host, or can be incorporated into a host, to deter insects/arthropods from approaching or remaining in the nearby 3-dimensional space in which the host exists. In either case, the effect of the repellent is to cause the insects/arthropds to reject the host, or to cause them to be driven out of and away from the host, which thereby minimizes the frequency of "bites" to an animate host, or minimizes the amount of damage that the insect/arthropod causes to an inanimate host. Repellents may be in the form of gases (olfactory), liquids, or solids (gustatory).

One property that is important to overall repellent effectiveness is surface activity, as many repellents contain both polar and non-polar regions in their structure. A second property is volatility. Repellents form an unusual class of compounds where evaporation of the active ingredient from a surface of, on or near a host makes an important contribution to its effectiveness, as measured by the protection of an animate host from bites or the protection of an inanimate host from damage.

An aspect of the potency of a repellent substance is the extent to which the concentration of the substance in the air space above or around a surface where it has been applied is sufficient to repel an insect or arthropod, particularly a flying insect. A desirable level of concentration of the repellent is obtained in the air space primarily from evaporation, but the rate of evaporation is affected by the rate of any absorption into the surface, and penetration into and through the surface is thus almost always an undesirable mode of loss of repellent from the surface. This consideration applies equally to the loss of a repellant by absorption into the skin or other surface of an animate host as to the loss of a repellant from a surface of an inanimate host made from a synthetic material, where the repellant substance may undesirably react with other chemicals present on that same surface. Loss of concentration of a repellant substance by physical action, such as dilution or absorption, or loss of concentration by chemical action, such as a reaction, is equally undesirable in the case of repellency of an insect/arthropod that crawls, for which concentration directly on a surface is an important factor.

In selecting a substance for use as an insect/arthropod repellent active, the inherent volatility of the substance thus is generally an important consideration. A variety of strategies are available, however, when needed for the purpose of attempting to increase persistence of the active while not decreasing, and preferably increasing, volatility. For example, the active can be formulated with polymers and inert ingredients to increase persistence on a surface to which applied or from which it will be exuded. The presence of inert ingredients in the formulation, however, dilutes the active in the formulation, and the loss of an active from undesirably rapid evaporation must thus be balanced against the risk of simply applying too little active to be effective. Alternatively, the active ingredient may be contained in microcapsules to control the rate of loss from a surface or an article; a precursor molecule, which slowly disintegrates on a surface or in an article, may be used to control the rate of release of the active ingredient; or a synergist may be used to continually stimulate the evaporation of the active from the formulated composition.

The release of an active ingredient that is intended for application to the skin or other surface of an animate host may be accomplished, for example, by sub-micron encapsulation, in which the active ingredient is encapsulated or enveloped in a skin-nourishing protein. The protein may be used, for example, at about a 20 wt % concentration. An application of repellent contains many of these protein capsules that may be suspended in either a water-based lotion, or water for spray application. After contact with skin, the protein capsules begin to break down, releasing the encapsulated active. The process continues as each microscopic capsule is depleted then replaced in succession by a new capsule that contacts the surface and releases its active ingredient. The process may take up to 24 hours for one application. Because a protein adheres very effectively to skin, these formulations are very resistant to perspiration (sweat-off) and dilution by water from other sources.

One of the distinct advantages of the preparations of this invention is that they are all characterized by a relative volatility that makes them suitable for use to obtain a desirably high level of concentration of active ingredient on, above and around a surface of an animate or inanimate host, as described above. One or more of these preparations may be used for such purpose as an active, or an active formulation, in a composition in which the preparation is admixed with a carrier suitable for wet or dry application of the composition to a surface in the form, for example, of a liquid, aerosol, gel, aerogel, foam or powder (such as a sprayable powder or a dusting powder). Suitable carriers include any one of a variety of commercially available organic and inorganic liquid, solid, or semi-solid carriers or carrier formulations usable in formulating a variety of cosmetic products. When formulating a composition for application to the skin or other surface of a human, it is important to select a dermatologically acceptable carrier. A carrier suitable for use herein may include water, alcohol, silicone, petrolatum, lanolin; or may include an organic liquid carrier such as a liquid aliphatic hydrocarbon (e.g. pentane, hexane, heptane, nonane, decane and their analogs) or a liquid aromatic hydrocarbon.

Examples of other useful liquid hydrocarbons include oils produced by the distillation of coal and the distillation of various types and grades of petrochemical stocks, including kerosene oils that are obtained by fractional distillation of petroleum. Suitable petroleum oils include those generally referred to as agricultural spray oils (e.g. the so-called light and medium spray oils, consisting of middle fractions in the distillation of petroleum and which are only slightly volatile). Such oils are usually highly refined and may contain only minute amounts of unsaturated compounds. Such oils, moreover, are generally paraffin oils and accordingly can be emulsified with water and an emulsifier, diluted to lower concentrations, and used as sprays. Tall oils, obtained from sulfate digestion of wood pulp, like the paraffin oils, can similarly be used. Other organic liquid carriers can include liquid terpene hydrocarbons and terpene alcohols such as alpha-pinene, dipentene, terpineol, and the like.

Other suitable carriers include silicone, petrolatum, lanolin, liquid hydrocarbons, agricultural spray oils, paraffin oil, tall oils, liquid terpene hydrocarbons and terpene alcohols, aliphatic and aromatic alcohols, esters, aldehydes, ketones, mineral oil, higher alcohols, finely divided organic and inorganic solid materials. In addition to the above-mentioned liquid hydrocarbons, the carrier can contain conventional emulsifying agents which can be used for causing the active ingredient to be dispersed in, and diluted with, water for end-use application. Still other liquid carriers can include organic solvents such as aliphatic and aromatic alcohols, esters, aldehydes, and ketones. Aliphatic monohydric alcohols include methyl, ethyl, normal-propyl, isopropyl, normal-butyl, sec-butyl, and tert-butyl alcohols. Suitable alcohols include glycols (such as ethylene and propylene glycol) and pinacols. Suitable polyhydroxy alcohols include glycerol, arabitol, erythritol, sorbitol, and the like. Finally, suitable cyclic alcohols include cyclopentyl and cyclohexyl alcohols.

Conventional aromatic and aliphatic esters, aldehydes and ketones can be used as carriers, and occasionally are used in combination with the above-mentioned alcohols. Still other liquid carriers include relatively high-boiling petroleum products such as mineral oil and higher alcohols (such as cetyl alcohol). Additionally, conventional or so-called "stabilizers" (e.g. tert-butyl sulfinyl dimethyl dithiocarbonate) can be used in conjunction with, or as a component of, the carrier or carriers used in a composition as made according to this invention.

Numerous clays having a layered structure with interstices, and synthetic inorganic materials that resemble such clays in respect of chemical composition, crystallinity and layered morphology, are suitable for use herein as carriers. Suitable clays having a layered structure with interstices include smectite, kaolin, muscovite, vermiculite, phlogopite, xanthophyllite, and chrysotile, and mixtures thereof. Preferred are smectite clays and kaolin clays. Smectite clays include montmorillonite, beidellite, nontronite, saponite, hectorite, sauconite, and others. Kaolin clays include kaolinite, deckite, nacrite, antigorite, and others. Most preferred is montmorillonite. Average particle sizes range from 0.5 to 50 micrometers.

Desirable properties of an insect/arthropod repellant composition, particularly one to be applied to the skin or other surface of an animate host, include low toxicity, resistance to loss by water immersion or sweating, low or no odor or at least a pleasant odor, ease of application, and rapid formation of a dry tack-free surface film. A composition possessing these properties enables treatment of a domesticated animal infested with an insect/arthropod (e.g. dogs infested with fleas, poultry infested with lice, or cattle infested with horn flies or ticks), or a human experiencing unavoidable exposure to an insect/arthropod, by contacting the skin, hide, hair, fur, feathers or other surface with an amount of the composition effective to repel the insect/arthropod from the host.

The application of an effective amount of an repellant composition on a surface subject to attack by an insect/arthropod (such as the skin, hide, hair, fur, or feathers of an animate host, or the stalks, stems, leaves or flowers of a plant or crop) may be accomplished by dispersing the composition into the air, or by dispersing the composition as a liquid mist or incorporated into a powder or dust, and this will permit the composition to fall on the desired surfaces of a host. It may also be desirable to formulate a repellent composition by combining a preparation hereof with a fugitive vehicle for application in the form of a spray. Such a composition may be an aerosol, sprayable liquid or sprayable powder composition adapted to disperse the active ingredient into the atmosphere by means of a compressed gas, or a mechanical pump spray. Likewise, directly spreading a liquid/semi-solid/solid repellent on a host in wet or dry form (as a friable solid, for example) is a useful method of contacting a surface of the host with an effective amount of the repellent.

Further, it may also be desirable to combine a preparation hereof with one or more other compounds known to have insect repellency in a composition to achieve a synergistic effect. Suitable insect repellant compounds combinable for such purpose include nepetalactones, nepetalactams, dihydronepetalactones and derivatives thereof, dihydronepetalactams and derivatives thereof, benzil, benzyl benzoate, 2,3,4, 5-bis(butyl-2-ene) tetrahydrofurfural, butoxypolypropylene glycol, N-butylacetanilide, normal-butyl-6,6-dimethyl-5,6-dihydro-1,4-pyrone-2-carboxylate, dibutyl adipate, dibutyl phthalate, di-normal-butyl succinate, N,N-diethyl-meta-toluamide, dimethyl carbate, dimethyl phthalate, 2-ethyl-2-butyl-1,3-propanediol, 2-ethyl-1,3-hexanediol, di-normal-propyl isocinchomeronate, 2-phenylcyclohexanol, p-methane-3,8-diol, and normal-propyl N,N-diethylsuccinamate.

In addition to one or more of the preparations hereof, an insect/arthropod repellent composition may also include one or more essential oils and/or active ingredients of essential oils. An essential oil includes any type of volatile oil that is obtained from a plant and possesses the odor and other characteristic properties of the plant. Examples of useful essential oils include: almond bitter oil, anise oil, basil oil, bay oil, caraway oil, cardamom oil, cedar oil, celery oil, chamomile oil, cinnamon oil, citronella oil, clove oil, coriander oil, cumin oil, dill oil, eucalyptus oil, fennel oil, ginger oil, grapefruit oil, lemon oil, lime oil, mint oil, parsley oil, peppermint oil, pepper oil, rose oil, spearmint oil (menthol), sweet orange oil, thyme oil, turmeric oil, and oil of wintergreen. Examples of active ingredients in essential oils are: citronellal, methyl salicylate, ethyl salicylate, propyl salicylate, citronellol, safrole, and limonene.

The insects and arthropods that may be repelled by the preparations hereof include any member of a large group of invertebrate animals characterized, in the adult state (non-adult insect states include larva and pupa) by division of the body into head, thorax, and abdomen, three pairs of legs, and, often (but not always) two pairs of membranous wings. This definition therefore includes a variety of biting insects (e.g. ants, bees, chiggers, fleas, mosquitoes, ticks, wasps), biting flies [e.g. black flies, green head flies, stable flies, horn flies (haematobia irritans)], wood-boring insects (e.g. termites), noxious insects (e.g. houseflies, cockroaches, lice, roaches, wood lice), and household pests (e.g. flour and bean beetles, dust mites, moths, silverfish, weevils).

In another embodiment, a preparation hereof may be used as a fragrance material or as an active in a fragrance composition, and be applied in a topical manner to human or animal skin or hair to impart a pleasing scent or aroma thereto, as in colognes or perfumes for humans or pets. Alternatively, the pleasing scent or aroma may be obtained by the use of a preparation hereof as an insect/arthropod repellant where the preparation has the dual attributes of simultaneously imparting both repellency as well as the pleasing scent or aroma.

In a further embodiment, the insect/arthropod repellency and/or fragrance of products directed to other fundamental purposes will be improved by the presence therein of a preparation of this invention. Those other products include, for example, a body wash, rinse, lotion, splash, tonic or toner, bath and shower gels, foam products (e.g. shaving foams), makeup, deodorants, shampoo, hair lacquers/hair rinses, personal soap compositions (e.g. hand soaps and bath/shower soaps) or other personal care treatments or palliatives, and cleaning agents such as detergents and solvents, and air fresheners and odor removers. Such products may be fabricated, for example, in the form of a sprayable liquid, an aerosol, a foam, a cream, an ointment, a gel, a paste, a powder or a friable solid. The process of fabricating such a product would thus include admixing a preparation hereof with suitable carriers or other inert ingredients to facilitate delivery in the physical form as described, such as liquid carriers that are readily sprayed; a propellant for an aerosol or a foam; viscous carriers for a cream, an ointment, a gel or a paste; or dry or semi-solid carriers for a powder or a friable solid.

Any of the above described products may also contain other therapeutically or cosmetically active adjuvants or supplemental ingredients as are typical in the personal care industry. Examples of these include fungicides, sunscreening agents, sunblocking agents, vitamins, tanning agents, plant extracts, anti-inflammatory agents, anti-oxidants, radical scavenging agents, retinoids, alpha-hydroxy acids, antiseptics, antibiotics, antibacterial agents, antihistamines; adjuvants such as thickeners, buffering agents, chelating agents, preservatives, gelling agents, stabilizers, surfactants, emolients, coloring agents, aloe vera, waxes, and penetration enhancers; and mixtures of any two or more thereof.

Inanimate hosts into which a preparation hereof may be incorporated to produce an insect/arthropod repellent effect, or to impart an improved fragrance, include articles or manufactured goods such as textile and fibrous goods, clothing, sanitary goods, carpeting, linens, outdoor or military equipment such as tents, tarpaulins, backpacks or mosquito netting, candles, paper, paint, ink, wood products such as furniture, plastics and other polymers, and the like.

A preparation hereof may be formulated as or incorporated into a composition for application to an animate host by any of the same methods known in the cosmetics industry, such as dilution, mixing, thickening, emulsifying, bottling and pressurizing. A preparation hereof may be incorporated into an article that serves as an inanimate host by mixing during production or by post-production steps such as spraying or dipping.

A preparation hereof may be admixed in a composition with other components, such as a carrier, in an amount that is effective for usage for a particular purpose, such as an insect/arthropod repellant, fragrance or other skin treatment. The amount of a puleganic amide as described herein, contained in a composition will generally not exceed about 80% by weight based on the weight of the final product, however, greater amounts may be utilized in certain applications, and this amount is not limiting. More preferably, a suitable amount of a puleganic amide will be at least about 0.001% by weight and preferably about 0.01% up to about 50% by weight; and more preferably, from about 0.01% to about 20% weight percent, based on the total weight of the total composition or article. Specific compositions will depend on the intended use.

Other compositions, materials and methods relevant to the use of a puleganic amide are as disclosed in U.S. 2003/062,357; U.S. 2003/079,786; U.S. 2003/191,047; and U.S. 2006/148,842, each of which is incorporated in its entirety as a part hereof for all purposes.

The present invention is further described in, but not limited by, the following specific embodiments.

EXAMPLES

General Procedures

The meaning of abbreviations used is as follows: "mL" means milliliter(s), "µL" means microliter, "g" means gram(s), "mg" means milligram, "kPa" means kilopascal, "MP" means melting point, "NMR" means nuclear magnetic resonance, "HPLC-MS" means high performance liquid chromatography-mass spectrometry, "GCMS" means gas chromatography-mass spectrometry, "° C." means degrees Centigrade, "RT" means room temperature (approximately 25° C.), "hr" means hour, and "ATP" means adenosine triphosphate.

All inorganic salts and organic solvents, with the exception of anhydrous terahydrofuran (THF), were obtained from VWR Scientific (West Chester, Pa). All other reagents used in the examples were obtained from Sigma-Aldrich Chemical (Milwaukee, Wis.) and used as received. Determination of pH was done with pHydrion paper from Micro Essential Laboratory, Inc. (Brooklyn, N.Y.). The puleganic amide products were purified by column chromatography on silica gel using ethyl acetate/hexanes as the eluant; the purified products were characterized by NMR spectroscopy. NMR spectra were obtained on a Bruker DRX Advance (500 MHz $^1$H, 125 MHz $^{13}$C; Bruker Biospin Corp., Billerica, Mass.) using deuterated solvents obtained from Cambridge Isotope Laboratories, Inc. (Andover, Mass.).

All reactions and manipulations related to the synthesis of the control and test repellents were carried out in a standard laboratory fume hood in standard laboratory glassware.

Purification of Trans, cis-nepetalactone:

Catmint oil (60 g) (Berjé; Bloomfield, N.J.; lot number 22941) containing approximately 75% trans, cis-nepetalactone (IIa) was placed into a 500 mL round-bottomed flask and treated with petroleum ether (200 mL) with stirring at RT. Upon cooling to 0° C., white solids precipitated from the solution and settled on the bottom of the flask. The white solids were filtered, washed with petroleum ether, cooled to 0° C. and dried under vacuum. The white solid product obtained (30 g, 50% yield) was determined to be trans, cis-nepetalactone by NMR analysis and gave a melting point of 27-29° C. (MP of 27.5-29° C., obtained from Sakan et al., *Tetrahedron Lett.* 1965, 4097-4101).

Synthesis of Puleganic Acid:
(1S,2R,5S)-2-isopropyl-5-methylcyclopentanecarboxylic acid (puleganic acid, Formula IV)

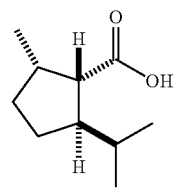

III is synthesized as follows: trans, cis-nepetalactone (30.0 g) was dissolved in 95% ethanol/5% isopropanol (300 mL) and placed in a Fisher-Porter bottle with 5% Pt/C (catalyst, 6.0 g). The tube was evacuated and backfilled with $H_2$ two times, then charged with $H_2$ at 30 psig (206.9 kPa). After stirring for 19 hr at room temperature, the tube was vented and the contents filtered over celite to remove catalyst. The solvent was removed under reduced pressure and the resulting residue was partitioned between hexanes (100 mL) and saturated sodium bicarbonate solution (150 mL). The aqueous layer was acidified with concentrated hydrochloric acid to pH=1.0. The mixture was then extracted three times with dichloromethane (50 mL), and the combined organic layers were dried over anhydrous sodium sulfate. Removal of the solvent under reduced pressure yielded puleganic acid as a clear oil (21.0 g, 68% yield). NMR analysis of the product obtained was consistent with the puleganic acid, (1S,2R,5S)-2-isopropyl-5-methylcyclopentanecarboxylic acid structure depicted in Formula III.

Example 1

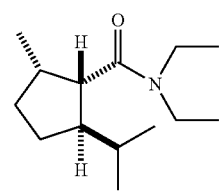

Ia

N,N-diethyl-(1S,2R,5S)-2-isopropyl-5-methylcyclopentanecarboxamide

Puleganic acid (III) (1.0 g) was dissolved in dichloromethane (10 mL) in a 100 mL round-bottomed flask under nitrogen and cooled to 0° C. with an ice bath. Triethylamine (0.82 mL) was added to the solution, followed by slow, dropwise addition of thionyl chloride (0.43 mL) via syringe. Separately, diethylamine (0.73 mL) was added to dichloromethane (5 mL) in a 100 mL round-bottomed flask under nitrogen and cooled to 0° C. The puleganic acid-triethylamine-thionyl chloride solution in the first flask was added drop-wise to the diethylamine solution via cannula under nitrogen at 0° C. After the addition was complete, the resulting solution was stirred at 0° C. for 30 minutes and then warmed to room temperature. After 30 minutes, the reaction solution was concentrated on a rotoevaporator, and the resulting residue was partitioned between dichloromethane (25 mL) and a 10% citric acid solution (25 mL). The layers were separated via a separatory funnel and the aqueous layer was re-extracted with dichloromethane (25 mL). The combined dichloromethane layers were washed with a saturated solution of sodium bicarbonate (30 mL) and dried over anhydrous sodium sulfate. Removal of the solvent under reduced pressure yielded the N,N-diethyl-puleganic amide as a pale yellow oil (0.95 g, 79% yield). NMR and GCMS analysis of the product obtained was consistent with the N,N-diethyl-(1S,2R,5S)-2-isopropyl-5-methylcyclopentanecarboxamide structure depicted in structural representation Ia in high purity.

Example 2

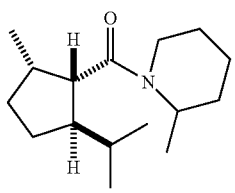

Ib

[(±)-2-methylpiperidinyl]-(1S,2R,5S)-2-isopropyl-5-methylcyclopentane-carboxamide The identical procedure described in Example 1 was employed using racemic 2-methylpiperidine (0.70 mL) in place of diethylamine which yielded (±)-2-methylpiperidinyl-puleganic amide as a clear oil (1.32 g, 86% yield). Purification of the crude reaction product was carried out by dissolving the crude reaction product obtained in dichloromethane (6 mL), followed by liquid-liquid extraction with a saturated sodium carbonate aqueous solution (10 mL). The separated organic layer was dried over anhydrous sodium sulfate and solvent was removed on the rotoevaporator to yield pure N-hexyl-puleganic amide as a white solid (381 mg, 26% yield). NMR and GCMS analysis of the product obtained was consistent with [(±)-2-methylpiperidinyl]-(1S,2R,5S)-2-isopropyl-5-methylcyclopentane-carboxamide.

Example 3

The products of Examples 1 and 2 were evaluated for insect repellency against *Aedes aegypti* mosquitoes in the in vitro landing assay. In this method a chamber contained 5 wells, each covered by a Baudruche (animal intestine) membrane. Each well was filled with bovine blood containing sodium citrate (to prevent clotting) and ATP (72 mg ATP disodium salt per 26 ml of blood), and heated to 37° C. A volume of 25 µL of isopropyl alcohol (IPA) containing one test specimen or control was applied to each membrane. The concentrations were 1.0% w/v in IPA. The negative control was neat IPA, and the positive control was a 1.0% w/v solution of DEET.

Figure 2:
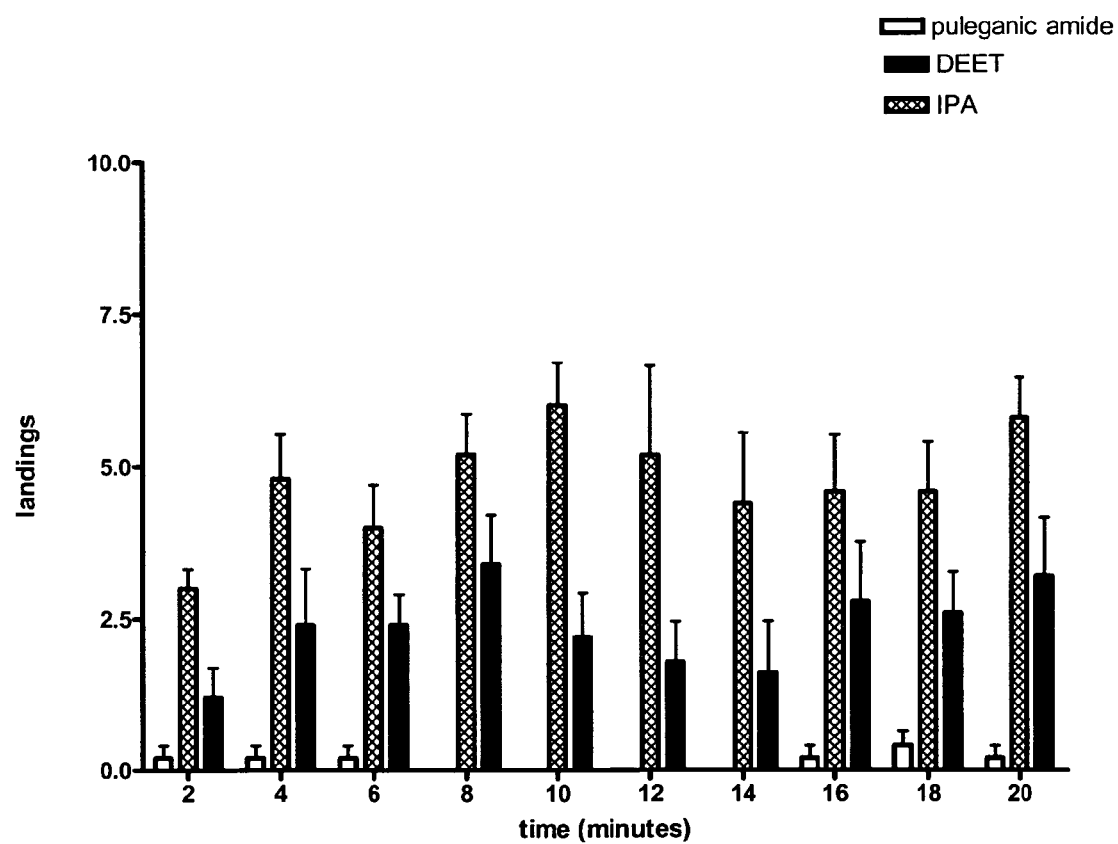

After 5 min, approximately 250 4-day-old female *Aedes aegypti* mosquitoes were introduced into the chamber. The number of mosquitoes probing the membranes for each treatment was recorded at 2 minute intervals over 20 min. The results for diethyl puleganic amide (Ia) and 2-methyl-piperidine puleganic amide (Ib) are depicted in FIGS. 1 and 2, respectively; each datum represents the mean of five replicate experiments.

Example 4

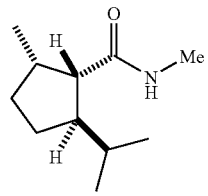

The identical procedure described in Example 1 was employed using methylamine (2.95 mL of a 2M solution in THF) in place of diethylamine which yielded N-methyl-puleganic amide as an oil (1.07 g, 82% yield). NMR analysis of the crude reaction product indicated puleganic acid was present. Purification of the crude reaction product by silica gel chromatography yielded pure N-methyl-puleganic amide as a white solid (204 mg, 19% yield). Analysis of the purified product by GCMS, HPLC-MS and NMR was consistent with the structural representation (shown above) of N-methyl-(1S,2R,5S)-2-isopropyl-5-methylcyclopentane-carboxamide (observed MP=133° C.)

Example 5

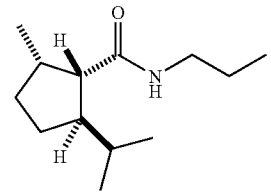

The identical procedure described in Example 1 was employed using propylamine (0.5 mL) in place of diethylamine which yielded propylpuleganic amide as an oil (1.24 g, 89% yield). NMR analysis of the crude reaction product indicated puleganic acid was present. Purification of the crude reaction product by silica gel chromatography yielded pure n-propyl-puleganic amide as a white solid (265 mg, 21% yield). Analysis of the purified product by GCMS, HPLC-MS and NMR was consistent with the structural representation (shown above) of N-propyl-(1S,2R,5S)-2-isopropyl-5-methylcyclopentane-carboxamide (observed MP=110° C.).

Example 6

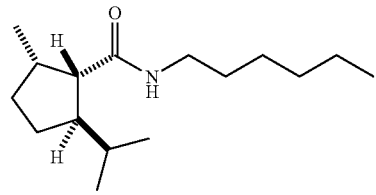

The identical procedure described in Example 1 was employed using hexylamine (0.8 mL) in place of diethylamine which yielded N-hexyl-puleganic amide as an oil (1.49 g, 83% yield). NMR analysis of the crude reaction product indicated puleganic acid was present. Purification of the crude reaction product was carried out by dissolving the crude reaction product obtained in dichloromethane (6 mL), followed by liquid-liquid extraction with a saturated sodium carbonate aqueous solution (10 mL). The separated organic layer was dried over anhydrous sodium sulfate and solvent was removed on the rotoevaporator to yield pure N-hexyl-puleganic amide as a white solid (485 mg, 33% yield). Analysis of the purified product by GCMS, HPLC-MS and NMR was consistent with the structural representation (shown above) of N-hexyl-(1S,2R,5S)-2-isopropyl-5-methylcyclopentane-carboxamide (observed MP=50.5° C.).

Example 7

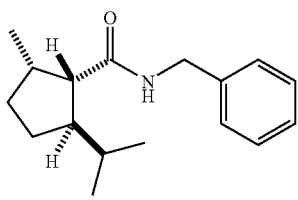

The identical procedure described in Example 1 was employed using benzylamine (0.64 mL) in place of diethylamine which yielded N-benzyl-puleganic amide as an oil (1.52 g, 87% yield). NMR analysis of the crude reaction product indicated puleganic acid was present. Purification of the crude reaction product by silica gel chromatography yielded pure N-benzyl-puleganic amide as a white solid (550 mg, 36% yield). Analysis of the purified product by GCMS, HPLC-MS and NMR was consistent with the structural representation (shown above) of N-benzyl-(1S,2R,5S)-2-isopropyl-5-methylcyclopentane-carboxamide (observed MP=114° C.).

Example 8

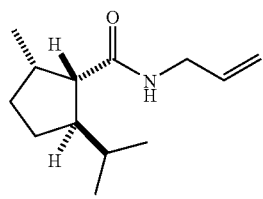

The identical procedure described in Example 1 was employed using allylamine (0.34 mL) in place of diethylamine which yielded N-allyl-puleganic amide as an oil (1.23 g, 85% yield). NMR analysis of the crude reaction product indicated puleganic acid was present. Purification of the crude reaction product by silica gel chromatography yielded pure N-allyl-puleganic amide as a white solid (310 mg, 25% yield). Analysis of the purified product by GCMS, HPLC-MS and NMR was consistent with the structural representation (shown above) of N-allyl- (1S,2R,5S)-2-isopropyl-5-methyl-cyclopentane-carboxamide (observed MP=89.50° C.).

What is claimed is:

1. A compound represented generally by the structure of the following Formula I

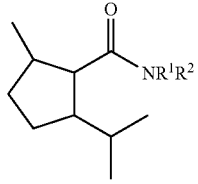

Formula I wherein $R^1$ and $R^2$ are each independently selected from the group consisting of:
   a) H, $CH_3$, $C_2H_5$;
   b) a $C_3$ to $C_{20}$ straight-chain, branched or cyclic alkane or alkene group; and
   c) a $C_3$ to $C_{20}$ straight-chain, branched or cyclic alkane or alkene group comprising a heteroatom selected from the group consisting of O, N and S;
provided that $R^1$ and $R^2$ are not both hydrogen; and wherein $R^1$ and $R^2$ may optionally together form a cyclic or bicyclic alkanyl or alkenyl group.

2. The compound of claim 1 wherein $R^1$ and $R^2$ are each independently selected from the group consisting of:
   1) a $C_3$ to $C_{12}$ straight-chain, branched or cyclic alkane or alkene group; and
   2) a $C_3$ to $C_{12}$ straight-chain, branched or cyclic alkane or alkene group comprising a heteroatom selected from the group consisting of O, N and S;
wherein $R^1$ and $R^2$ can optionally together form a cyclic or bicyclic alkanyl or alkenyl group.

3. The compound of claim 1 which is N,N-diethyl-(1S,2R,5S)-2-isopropyl-5-methylcyclopentanecarboxamide or [(±)-2-methylpiperidinyl]-(1S,2R,5S)-2-isopropyl-5-methylcyclopentane-carboxamide.

4. The compound of claim 1 which is a single stereoisomer of the Formula I compound or is a combination of stereoisomers of the Formula I compound.

5. A composition of matter comprising (a) one or both of a carrier and a cosmetic or therapeutic adjuvant, and (b) a compound described generally by the structure of the following Formula I

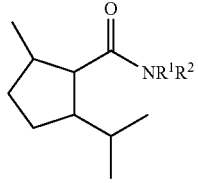

Formula I wherein $R^1$ and $R^2$ are each independently selected from the group consisting of:
   a) H, $CH_3$, $C_2H_5$;
   b) a $C_3$ to $C_{20}$ straight-chain, branched or cyclic alkane or alkene group; and
   c) a $C_3$ to $C_{20}$ straight-chain, branched or cyclic alkane or alkene group comprising a heteroatom selected from the group consisting of O, N and S;
provided that $R^1$ and $R^2$ are not both hydrogen; wherein $R^1$ and $R^2$ may optionally together form a cyclic or bicyclic alkanyl or alkenyl group.

6. The composition of claim 5 wherein the compound of Formula I is a single stereoisomer of the compound, or is a mixture of stereoisomers of the compound.

7. The composition of claim 5 further comprising a dihydronepetalactone.

8. The composition of claim 5 further comprising an essential oil.

9. The composition of claim 5 wherein an adjuvant comprises any one or more members of the group consisting of fungicides, sunscreening agents, sunblocking agents, vitamins, tanning agents, plant extracts, anti-inflammatory agents, anti-oxidants, radical scavenging agents, retinoids, alpha-hydroxy acids, antiseptics, antibiotics, antibacterial agents, antihistamines; thickeners, buffering agents, chelating agents, preservatives, gelling agents, stabilizers, surfactants, emolients, coloring agents, aloe vera, waxes, and penetration enhancers.

10. The composition of claim 5 which comprises the compound of Formula I in an amount of from about 0.001% to about 80% by weight of the total weight of the composition.

11. The composition of claim 5 in the form of a sprayable liquid, an aerosol, a foam, a cream, an ointment, a gel, a paste, a powder or a friable solid.

12. A method of repelling an insect or arthropod comprising exposing the insect or arthropod to a compound described generally by the structure of the following Formula I:

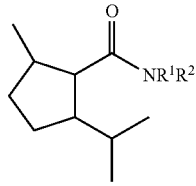

Formula I wherein $R^1$ and $R^2$ are each independently selected from the group consisting of:
a) H, $CH_3$, $C_2H_5$;
b) a $C_3$ to $C_{20}$ straight-chain, branched or cyclic alkane or alkene group; and
c) a $C_3$ to $C_{20}$ straight-chain, branched or cyclic alkane or alkene group comprising a heteroatom selected from the group consisting of O, N and S;
provided that $R^1$ and $R^2$ are not both hydrogen; wherein $R^1$ and $R^2$ may optionally together form a cyclic or bicyclic alkanyl or alkenyl group.

13. The method of claim 12 wherein the compound of Formula I is a single stereoisomer of the compound, or is a mixture of stereoisomers of the compound.

14. The method of claim 12 which comprises exposing the insect or arthropod to a composition that comprises the compound of Formula I in an amount of from about 0.001% to about 80% by weight of the total weight of the composition.

15. The method of claim 14 wherein the composition comprises one or both of a carrier or a cosmetic or therapeutic adjuvant.

16. The method of claim 14 wherein the composition 1 further comprises a dihydronepetalactone.

17. The method of claim 14 wherein the composition further comprises an essential oil.

18. The method of claim 14 wherein the composition comprises an adjuvant selected from any one or more members of the group consisting of fungicides, sunscreening agents, sunblocking agents, vitamins, tanning agents, plant extracts, anti-inflammatory agents, anti-oxidants, radical scavenging agents, retinoids, alpha-hydroxy acids, antiseptics, antibiotics, antibacterial agents, antihistamines; thickeners, buffering agents, chelating agents, preservatives, gelling agents, stabilizers, surfactants, emolients, coloring agents, aloe vera, waxes, and penetration enhancers.

19. The method of claim 12 which comprises exposing a blood-feeding insect or arthropod to the compound.

20. The method of claim 14 which comprises exposing a blood-feeding insect or arthropod to the composition.

21. The method of claim 12 which comprises exposing an insect or arthropod selected from the group consisting of biting flies, chiggers, fleas, mosquitoes, ticks and lice to the compound.

22. The method of claim 14 which comprises exposing an insect or arthropod selected from the group consisting of biting flies, chiggers, fleas, mosquitoes, ticks and lice to the composition.

23. The method of claim 12 which comprises applying the compound to the skin, hide, hair, feathers or fur or other surface of a host for an insect or arthropod.

24. The method of claim 14 which comprises applying the composition to the skin, hide, hair, feathers or fur or other surface of a host for an insect or arthropod.

25. A method for making a composition of matter that may be applied to the skin, hide, hair, feathers or fur or other surface of a human or domesticated animal comprising admixing (a) one or both of a carrier and a cosmetic or therapeutic adjuvant with (b) a compound described generally by the structure of the following Formula I:

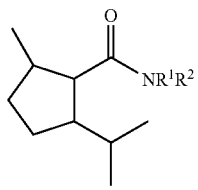

Formula I wherein $R^1$ and $R^2$ are each independently selected from the group consisting of:
a) H, $CH_3$, $C_2H_5$;
b) a $C_3$ to $C_{20}$ straight-chain, branched or cyclic alkane or alkene group; and
c) a $C_3$ to $C_{20}$ straight-chain, branched or cyclic alkane or alkene group comprising a heteroatom selected from the group consisting of O, N and S;
provided that $R^1$ and $R^2$ are not both hydrogen; wherein $R^1$ and $R^2$ may optionally together form a cyclic or bicyclic alkanyl or alkenyl group.

26. The method of claim 25 wherein the compound of Formula I is a single stereoisomer of the compound, or is a mixture of stereoisomers of the compound.

27. The method of claim 25 further comprising a step of preparing the compound of Formula I from nepetalactone.

28. The method of claim 25 wherein the composition further comprising a dihydronepetalactone.

29. The method of claim 25 wherein the composition further comprises an adjuvant selected from any one or more members of the group consisting of fungicides, sunscreening agents, sunblocking agents, vitamins, tanning agents, plant extracts, anti-inflammatory agents, anti-oxidants, radical scavenging agents, retinoids, alpha-hydroxy acids, antiseptics, antibiotics, antibacterial agents, antihistamines; thickeners, buffering agents, chelating agents, preservatives, gelling agents, stabilizers, surfactants, emolients, coloring agents, aloe vera, waxes, and penetration enhancers.

30. The method of claim 25 wherein the composition comprises the compound of Formula I in an amount of from about 0.001% to about 80% by weight of the total weight of the composition.

31. The method of claim 25 further comprising a step of fabricating the composition in the form of a sprayable liquid, an aerosol, a foam, a cream, an ointment, a gel, a paste, a powder or a friable solid.

32. The compound of claim 1 wherein, on the cyclopentyl ring, the methyl group and the amide group are both in the S stereochemical configuration.

33. The composition of claim 5 wherein, on the cyclopentyl ring, the methyl group and the amide group are both in the S stereochemical configuration.

34. The method of claim 12 wherein, on the cyclopentyl ring, the methyl group and the amide group are both in the S stereochemical configuration.

35. The method of claim 25 wherein, on the cyclopentyl ring, the methyl group and the amide group are both in the S stereochemical configuration.

36. A process for preparing a compound represented by the structure of the following Formula I

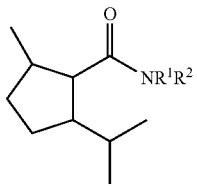

Formula I wherein $R_1$ and $R_2$ are each independently selected from the group consisting of:
  a) H, $CH_3$, $C_2H_5$;
  b) a $C_3$ to $C_{20}$ straight-chain, branched or cyclic alkane or alkene group;
  c) a $C_3$ to $C_{20}$ straight-chain, branched or cyclic alkane or alkene group comprising a heteroatom selected from the group consisting of O, N and S;
  d) an unsubstituted or substituted $C_6$ to $C_{20}$ aromatic group, wherein the substituent is selected from the group consisting of a $C_1$ to $C_{12}$ straight-chain, branched or cyclic alkane or alkene group; and
  e) an unsubstituted or substituted $C_6$ to $C_{20}$ aromatic group comprising a heteroatom selected from the group consisting of O, N and S, wherein the substituent is selected from the group consisting of a $C_1$ to $C_{12}$ straight-chain, branched or cyclic alkane or alkene group;
provided that (i) $R^1$ and $R^2$ are not both hydrogen, and (ii) that when $R^1$ is methyl, $R^2$ is not phenyl; wherein $R^1$ and $R^2$ may optionally together form a cyclic or bicyclic alkanyl or alkenyl group; and comprising:
  (a) hydrogenating a nepetalactone to form a nepetalic acid; and
  (b) contacting the nepetalic acid with an amine represented by the formula $NHR^1R^2$.

37. A process according to claim 36 wherein, on the cyclopentyl ring, the methyl group and the amide group are both in the S stereochemical configuration.

38. A process according to claim 36 wherein the nepetalactone is a trans, cis-nepetalactone.

39. A process according to claim 36 wherein the nepetalactone is a cis, trans-nepetalactone.

40. A process according to claim 36 wherein $R^1$ and $R^2$ are each independently selected from the group consisting of:
  a) H, $CH_3$, $C_2H_5$;
  b) a $C_3$ to $C_{20}$ straight-chain, branched or cyclic alkane or alkene group; and
  c) a $C_3$ to $C_{20}$ straight-chain, branched or cyclic alkane or alkene group comprising a heteroatom selected from the group consisting of O, N and S;
provided that $R^1$ and $R^2$ are not both hydrogen; and wherein $R_1$ and $R_2$ may optionally together form a cyclic or bicyclic alkanyl or alkenyl group.

41. A compound represented by the structure of the following formula:

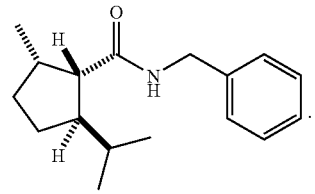

* * * * *